US012766283B2

(12) United States Patent
(10) Patent No.: US 12,766,283 B2
(45) Date of Patent: Oct. 20, 2026

Schwaibold et al.

(54) RESPIRATORY GAS SUPPLY SYSTEM

(71) Applicant: Loewenstein Medical Technology S.A., Luxembourg (LU)

(72) Inventors: Matthias Schwaibold, Karlsruhe (DE); Mario Scheerer, Baden-Baden (DE); Christof Schroeter, Karlsbad (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1719 days.

(21) Appl. No.: 16/202,260

(22) Filed: Nov. 28, 2018

(65) Prior Publication Data

US 2019/0160242 A1 May 30, 2019

(30) Foreign Application Priority Data

Nov. 30, 2017 (DE) ......................... 102017011088.3

(51) Int. Cl.
*A61M 16/00* (2006.01)
*A61M 16/04* (2006.01)
(Continued)

(52) U.S. Cl.
CPC ...... *A61M 16/024* (2017.08); *A61M 16/0465* (2013.01); *A61M 16/0666* (2013.01);
(Continued)

(58) Field of Classification Search
CPC ............ A61M 16/024; A61M 16/0465; A61M 16/0666; A61M 16/08; A61M 16/1075; A61M 16/16; A61M 16/04; A61M 16/0672; A61M 16/12; A61M 16/125; A61M 16/14; A61M 16/20; A61M 2016/0027; A61M 2016/003; A61M 2016/0033; A61M 2016/0039; A61M 2016/0042; A61M 2202/0208; A61M 2202/0216;
(Continued)

(56) References Cited

U.S. PATENT DOCUMENTS 5,896,857 A * 4/1999 Hely ........................ A62B 9/02 128/205.24
6,532,960 B1 * 3/2003 Yurko ................. A61M 16/024 128/204.23
(Continued)

FOREIGN PATENT DOCUMENTS

EP 2181726 A1 5/2010
WO 2009146484 A1 12/2009
(Continued)

*Primary Examiner* — LaToya M Louis
(74) *Attorney, Agent, or Firm* — Abel Schillinger, LLP

(57) ABSTRACT

Disclosed is a respiratory gas supply system comprising a respiratory gas source, a control unit, a pressure control module, a flow control module, a pressure sensor device, a flow sensor device and a user interface for the specification of respiratory gas supply parameters or for the exchange of data. The control unit alternately activates the pressure control module and the flow control module, with the pressure control module controlling the respiratory gas source to specify a respiratory gas pressure in the range of 0-90 mbar and the flow control module controlling the respiratory gas source to specify a respiratory gas flow in the range of 0-90 l/min.

13 Claims, 6 Drawing Sheets

(51) Int. Cl.

| | |
|---|---|
| ***A61M 16/06*** | (2006.01) |
| ***A61M 16/08*** | (2006.01) |
| ***A61M 16/10*** | (2006.01) |
| ***A61M 16/16*** | (2006.01) |
| *A61M 16/12* | (2006.01) |
| *A61M 16/14* | (2006.01) |
| *A61M 16/20* | (2006.01) |

(52) U.S. Cl.
CPC ........ *A61M 16/08* (2013.01); *A61M 16/1075* (2013.01); *A61M 16/16* (2013.01); *A61M 2016/0027* (2013.01); *A61M 2016/003* (2013.01); *A61M 2016/0033* (2013.01); *A61M 2016/0039* (2013.01); *A61M 2016/0042* (2013.01); *A61M 16/04* (2013.01); *A61M 16/0672* (2014.02); *A61M 16/12* (2013.01); *A61M 16/125* (2014.02); *A61M 16/14* (2013.01); *A61M 16/20* (2013.01); *A61M 2202/0208* (2013.01); *A61M 2202/0216* (2013.01); *A61M 2205/18* (2013.01); *A61M 2205/502* (2013.01)

(58) Field of Classification Search
CPC ........ A61M 2205/18; A61M 2205/502; A61M 16/0003; A61M 16/10; A61M 2205/3331
See application file for complete search history.

(56) References Cited

U.S. PATENT DOCUMENTS

| | | | | |
|---|---|---|---|---|
| 2005/0166922 | A1* | 8/2005 | Knepper ............. | A61M 16/024 128/204.23 |
| 2007/0215146 | A1* | 9/2007 | Douglas ............ | A61M 16/0051 128/200.24 |
| 2008/0000475 | A1 | 1/2008 | Hill | |
| 2009/0090363 | A1* | 4/2009 | Niland ................ | A61M 16/122 128/203.26 |
| 2009/0151719 | A1 | 6/2009 | Wondka | |
| 2011/0253136 | A1 | 10/2011 | Sweeney | |
| 2012/0017909 | A1* | 1/2012 | Porges ................ | A61M 16/125 128/205.25 |
| 2012/0291783 | A1 | 11/2012 | Peiris | |
| 2013/0133656 | A1* | 5/2013 | Nightingale ......... | A61B 5/4809 128/204.23 |
| 2017/0274165 | A1 | 9/2017 | Ramanan et al. | |
| 2018/0085544 | A1 | 3/2018 | Holyoake | |

FOREIGN PATENT DOCUMENTS

| | | | |
|---|---|---|---|
| WO | 2011068418 | A1 | 6/2011 |
| WO | 2016157105 | A1 | 10/2016 |

* cited by examiner

RESPIRATORY GAS SUPPLY SYSTEM

CROSS-REFERENCE TO RELATED APPLICATIONS

The present application claims priority under 35 U.S.C. § 119 of German Patent Application No. 102017011088.3, filed Nov. 30, 2017, the entire disclosure of which is expressly incorporated by reference herein.

BACKGROUND OF THE INVENTION

1. Field of the Invention

The invention relates to a respiratory gas supply system comprising a respiratory gas source, a control unit, a pressure control module and a flow control module, wherein a pressure sensor device, and a flow sensor device, and a user interface are also provided for the specification of parameters of the respiratory gas supply or for the exchange of data. The control unit alternately activates the pressure control module and the flow control module, wherein the pressure control module controls the respiratory gas source so as to specify a respiratory gas pressure, and the flow control module controls the respiratory gas source so as to specify a respiratory gas flow.

2. Discussion of Background Information

Pressure-Assisted and Pressure-Controlled Respiration

In pressure-assisted respiration, the patient's respiratory drive is—more or less—taken into account. In contrast to volume-controlled respiration, it is gentler, since no high peak pressures can occur here. When the patient inhales, the respiratory process is supported and respiration is facilitated. Pressure-assisted respiration is characterized by a lower pressure level and an upper pressure level. These two pressures are variably adjustable. The quantity of air that is released until the upper pressure is reached defines the respiratory volume. If the patient has longer pauses in respiration, he or she can be intermediately respirated in a controlled manner by means of a backup/background frequency. The triggering of inspiration and expiration can be flow controlled, or pressure controlled, or time controlled.

In CPAP therapy, a patient's spontaneous respiration is supported by a continuous positive pressure to prevent respiratory arrests.

Volume-Controlled Respiration

In this form of respiration, a fixed respiratory volume is applied to the patient within a specified inspiration time. The respiratory volume per minute is calculated from the respiratory volume and the respiratory frequency. High peak pressures can occur with this type of respiration, as the respirator primarily attempts to apply the set volume. To prevent this risk, a maximum pressure must be stored as an alarm limit.

Mixed forms of the aforementioned respiration modes attempt to combine the "advantages" of both forms of respiration (volume and pressure respiration).

There is still no known system for respiratory gas supply or known respiratory gas source that provides a high flow and alternately a pressure-supported or pressure-controlled respiration.

SUMMARY OF THE INVENTION

The present invention provides a respiratory gas supply system comprising a respiratory gas source, a control unit, a memory, a pressure control module and a flow control module, a pressure sensor device and a flow sensor device, and a user interface for the specification of respiratory gas supply parameters or for the exchange of data, including a respiratory gas tube and a patient interface. The system additionally comprises at least a humidifier and/or an oxygen source and/or a nebulizer and/or a heater. Further, the control unit alternately activates the pressure control module or the flow control module, the pressure control module controlling the respiratory gas source for the specification of a respiratory gas pressure, and the flow control module controlling the respiratory gas source for the specification of a respiratory gas flow.

The system may further be characterized in that when the flow control module 6 is activated, the control unit additionally activates the humidifier 13 and the heater 16 so as to heat and humidify the respiratory gas.

The system may alternatively or additionally be characterized in that when the flow control module 6 is activated, the control unit additionally activates the humidifier 13, and the heater 16, and the oxygen source 14 for purposes of conditioning the respiratory gas.

The system may alternatively or additionally be characterized in that the flow control module 6 controls the respiratory gas source 2 so as to specify a respiratory gas flow in the range of 0-90 l/min, preferably 1-80 l/min, particularly preferably 2-60 l/min.

The system may alternatively or additionally be characterized in that the pressure control module 4 controls the respiratory gas source 2 so as to specify a respiratory gas pressure in the range of 0-90 mbar, preferably 1-80 mbar, particularly preferably 2-60 mbar.

The system may alternatively or additionally be characterized in that the pressure control module 4 controls the respiratory gas source so as to specify a low expiratory pressure and a higher inspiratory pressure.

The system may alternatively or additionally be characterized in that the pressure control module 4 controls the respiratory gas source so as to specify a constant pressure.

The system may alternatively or additionally be characterized in that the pressure control module alternately controls the respiratory gas source so as to specify a low expiratory pressure and a higher inspiratory pressure and a constant pressure.

The system may alternatively or additionally be characterized in that the pressure control module controls the respiratory gas source so as to specify a constant inspiratory pressure.

The system may alternatively or additionally be characterized in that the pressure control module controls the respiratory gas source so as to specify an inspiratory pressure with a prescribable pressure waveform.

The system may alternatively or additionally be characterized in that the pressure control module controls the respiratory gas source so as to specify an inspiratory pressure with two different inspiratory pressure levels.

The system may alternatively or additionally be characterized in that the pressure control module controls the respiratory gas source so as to specify a constant expiratory pressure.

The system may alternatively or additionally be characterized in that the pressure control module controls the respiratory gas source so as to specify an expiratory pressure with a prescribable pressure waveform.

The system may alternatively or additionally be characterized in that the pressure control module controls the respiratory gas source so as to specify an expiratory pressure with two different expiratory pressure levels, the pressure being raised from a low expiratory level to an increased expiratory level.

The system may alternatively or additionally be characterized in that the pressure control module controls the respiratory gas source so as to specify an expiratory pressure and a ramp-form pressure rise to an inspiratory pressure level.

The system may alternatively or additionally be characterized in that the pressure control module controls the respiratory gas source so as to specify an inspiratory pressure and a ramp-form pressure drop to an expiratory pressure level.

The system may alternatively or additionally be characterized in that the control unit is designed to detect respiratory efforts from the pressure signal, and/or from the flow signal of the pressure sensor device and/or the flow sensor device.

The system may alternatively or additionally be characterized in that the respiratory gas source is designed as an electric motor with a fan rotor.

The system may alternatively or additionally be characterized in that the patient interface is designed as a nasal cannula, or a flow cannula, or a mask, or as a tracheostomy port.

The system may alternatively or additionally be characterized in that when the flow control module is activated, a nasal cannula, or flow cannula, or a tracheostomy port, is used as the patient interface.

The system may alternatively or additionally be characterized in that when the flow control module is activated an internal or external humidifier is also activated.

The system may alternatively or additionally be characterized in that the control unit controls the respiratory gas source during the day for the specification of a respiratory gas flow and at night for the specification of a respiratory gas pressure, with a low inspiratory pressure and a higher expiratory pressure.

The system may alternatively or additionally be characterized in that the control unit controls the respiratory gas source during the day for the specification of a respiratory gas flow and at night for the specification of at least one respiratory gas pressure level which is modulated as a function of signals from the pressure sensor device and/or the flow sensor device, if the signals are indicative of periodic respiration or of interrupted respiration.

The system may alternatively or additionally be characterized in that the control unit controls the respiratory gas source during the day for the specification of a respiratory gas flow and at night for the specification of at least one respiratory gas pressure level which is modulated as a function of signals from the pressure sensor device and/or the flow sensor device if the signals are indicative of periodic respiration or of interrupted respiration.

The system may alternatively or additionally be characterized in that the control unit 3 controls the respiratory gas source 2 so as to specify a prescribable respiratory gas flow, and increases the pressure as a function of signals 20 of the pressure sensor device 7 and/or the flow sensor device 8 until the specified respiratory gas flow is reached.

The system may alternatively or additionally be characterized in that the control unit 3 controls the respiratory gas source 2 so as to specify a prescribable respiratory gas flow, wherein the flow sensor device 8 monitors the respiratory gas flow, wherein the control unit checks whether the prescribed respiratory gas flow has been reached on the basis of the signals of the flow sensor device 8, wherein the pressure sensor device monitors the respiratory gas pressure, wherein the control unit uses the signals from the pressure sensor device to check whether a prescribed maximum respiratory gas pressure has been reached, and the control unit does not further increase the maximum respiratory gas pressure if the prescribed respiratory gas flow has not been reached.

The system may alternatively or additionally be characterized in that the control unit activates the flow control module 6 and thereby attempts to generate the set flow, and thereby also determines the pressure required for it; if this reaches a prescribed threshold for a period of, typically approx. 0.001-10 seconds, the control unit then switches to pressure control 4, and maintains a prescribed maximum permissible pressure, even if the flow is below the prescribed specified value, if the set flow is again reached or exceeded, for a period of, typically approx. 0.001-10 seconds, the control unit then again switches back to the flow control 6.

The system may also be used for mixing ambient air (under flow) and oxygen ($O_2$).

The quantity of respiratory gas supplied may be controlled by a flow meter (1-90 l/min). In addition, the application of the desired quantity of oxygen (up to 100%) may be adjusted via an oxygen mixer.

The respiratory gas may be supplied to the patient via a special nasal cannula, which serves to support spontaneous respiration.

By virtue of the high gas flow, a positive airway pressure (PEEP) is created, which depends on the level of the gas flow. By virtue of the high gas flow, carbon dioxide is washed out of the nasopharynx.

The high gas flow enables an earlier extubation (removal of the respiration tube).

The high gas flow makes the respiration easier. The high gas flow minimizes the respiratory effort. The respiratory rate is reduced by high flow rates.

The invention also provides a respiratory gas source 2, which comprises a control unit 3, a memory 5, a pressure control module 4 and a flow control module 6, a pressure sensor device 7 and a flow sensor device 8, and a user interface 9, for the specification of parameters 10 of the respiratory gas supply or for the exchange of data, with a respiratory gas tube 11 and a patient interface 12. The system 1 additionally comprises at least one humidifier 13 and/or an oxygen source 14 and/or a nebulizer 15 and/or a heater 16. Further, the control unit 3 alternately activates the pressure control module 4 or the flow control module 6, the pressure control module 4 controlling the respiratory gas source 2 so as to specify a respiratory gas pressure, and the flow control module 6 controlling the respiratory gas source so as to specify a respiratory gas flow.

BRIEF DESCRIPTION OF THE DRAWINGS

Further benefits and features of the present invention will emerge from the description of exemplary embodiments, which will be explained with reference to the accompanying drawings.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
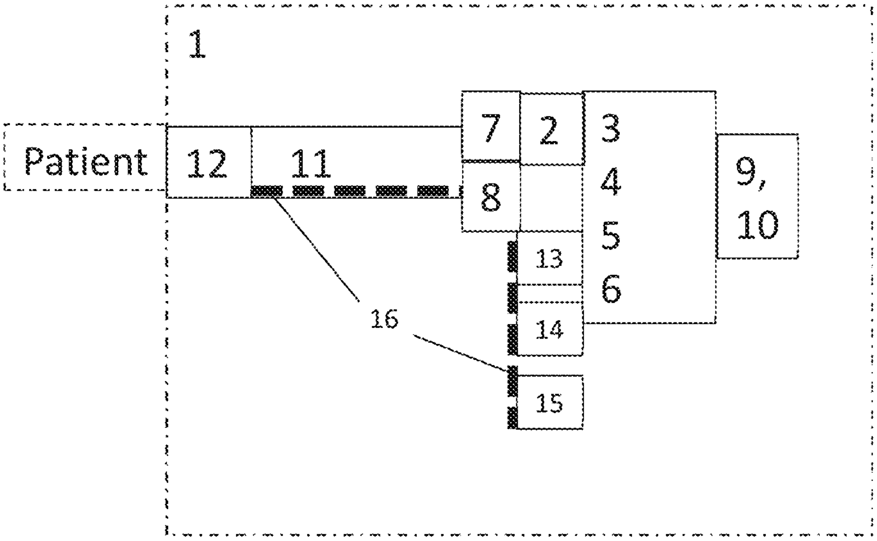
FIG. 1 shows schematically a respiratory gas supply system according to the instant invention.

FIG. 1 shows schematically the respiratory gas supply system 1, comprising a respiratory gas source 2, a control unit 3, a pressure control module 4, a flow control module 6 and a memory 5, wherein a pressure sensor device 7 and a flow sensor device 8 and a user interface 9 are also included for the specification of parameters 10 of the respiratory gas supply or for the exchange of data. The system comprises a respiratory gas tube 11 and a patient interface 12, wherein the system 1 additionally has at least one humidifier 13 and/or an oxygen source 14 and/or a nebulizer 15 and/or a heater 16. The control unit 3 alternately activates the pressure control module 4 and the flow control module 6, wherein the pressure control module 4 controls the respiratory gas source 2 so as to specify a respiratory gas pressure in the range of 0-90 mbar and wherein the flow control module 6 controls the respiratory gas source so as to specify a respiratory gas flow in the range of 0-90 l/min.

The control unit 3 is set up and designed to control the respiratory gas source 2, using the pressure control module 4 or the flow control module 6, for the automatic specification of a respiratory gas pressure and/or a respiratory gas flow.

When the flow control module 4 is activated the control unit 3 is also set up and designed to activate, at least temporarily, the humidifier 13 or the nebulizer and the heater 16 for heating and humidifying the respiratory gas.

When the flow control module 4 is activated, the control unit 3 can also activate an oxygen source 14 and/or a nebulizer 15 for purposes of conditioning the respiratory gas.

The respiratory gas tube 11 and/or the humidifier 13 and/or the nebulizer 15 each have a heater 16. Alternatively, at least the respiratory gas tube 11 and/or the humidifier 13 and/or the nebulizer 15 has a heater 16.

The control unit is equipped and designed to detect respiratory efforts from the pressure signal and/or the flow signal of the pressure sensor device and/or the flow sensor device. The control unit is also equipped and designed to detect periodic respiration or interrupted respiration from the pressure signal and/or from the flow signal of the pressure sensor device and/or the flow sensor device.

The user interface 9 for the specification of parameters 10 of the respiratory gas supply or for the exchange of data is designed, for example, as a touch screen. Alternatively or additionally, a display and input keys can also be provided. In addition, the user interface 9 has at least one interface (USB, Bluetooth, WLAN . . . ) for connecting external devices or a network for the exchange of data. Prescribed parameters are stored in the memory such that they can be called up.

The respiratory gas source 2, for example, is designed as an electric motor with a fan rotor or as a compressed gas source. The patient interface 12 is designed as a nasal cannula, or a mask, or as a tracheostomy port.

The system is designed and configured such that when the flow control module is activated, a nasal cannula or tracheostomy port is used as the patient interface, and when the flow control module is activated, an internal or external humidifier is also activated and used.

The system is designed and set up, for example, to deactivate the internal humidifier when the flow control module is activated. Instead, an external humidifier is used or activated that is more powerful.

The system is designed and set up, for example, to deactivate an internal oxygen source 14 when the flow control module is activated. Instead, an external oxygen source is used.

The system is designed and set up, for example, such that when the flow control module is activated, oxygen is added up to 90 l/min via an internal or external oxygen source.

The system is designed and set up, for example, such that when the flow control module is activated, the control unit, taking into account the signals from the flow and/or pressure sensor device, activates an oxygen source for an oxygen admixture that is modulated as a function of the respiratory phase. For example, the intention is to control the oxygen admixture in such a way that more oxygen is available to the patient during phases of inspiration than for expiration.

For example, the system is designed and set up such that a pulse oximeter 17 or a $CO_2$ measuring device 18 can be adapted, which then communicates with the system and/or is supplied with energy by the latter. Using the measured values from these devices, the user—or an automatic algorithm—can set the correct flow rate and the correct oxygen admixture. For example, the control unit takes into account measured values from the pulse oximeter 17 and/or the $CO_2$ meter 18 when activating/controlling the oxygen source and/or activating/controlling the flow control module 6.

In accordance with the invention, it is intended that the user should enter a specification into the control unit 3 via the user interface to activate the pressure control module or the flow control module 6. The specification can also be stored in the memory and read out by the control unit. In accordance with the invention, it is also intended that the control unit 3 should automatically select module 4 or 6 on the basis of information stored in the memory, and should control the latter by specifying the parameters (pressure values, flow values . . . ).

In accordance with the invention, it is also intended that the control unit 3 should select module 4 or 6 on the basis of a time setting, and should control the latter by specifying the parameters.

In accordance with the invention, it is also intended that the control unit 3 should determine which patient interface is adapted, and should activate the appropriate module on the basis of this information.

In accordance with the invention, it is also intended that the control unit 3 should determine which patient interface is adapted, and should compare whether the patient interface matches the activated module, and should either automatically activate the appropriate module, or should activate an alarm to inform the user of an incompatible combination of patient interface and module.

For example, the system detects whether a valve respiration tube is connected or not. It recognizes this by whether it can build up and measure a pressure in the control lines for the valve. If a valve respiratory tube is used, the control unit does not activate the flow control module 6.

In accordance with the invention, it is also intended that the control unit should activate the flow control module 6 and thereby determine which pressure fluctuations in the tube are triggered by the patient's respiration. If these are greater than a defined threshold value, the control unit determines therefrom that the patient interface is too tightly sealed or unsuitable. Thus, for example, a mask or tracheostomy port is adapted, but not a nasal cannula. A corresponding message or alarm will then be issued. The control unit could then also deactivate the flow control module 6.

In accordance with the invention, it is also intended that the control unit should activate the flow control module 6 and thereby attempt to generate the set flow and also determine the required pressure. If it reaches a prescribed threshold for a period of time, typically approx. 0.001-10 seconds, the control unit switches to pressure control 4 and maintains a prescribed maximum permissible pressure, even if the flow is below the specified value. If the set flow is reached or exceeded again for a period of time, typically approx. 0.001-10 seconds, the device then again switches back to flow control 6.

In accordance with the invention, it is also intended that the control unit should activate the flow control module 6 and thereby determine which respiratory phases are present. The control unit detects fluctuations caused by respiration and attempts to compensate for these on a continuous basis.

Figure 2:
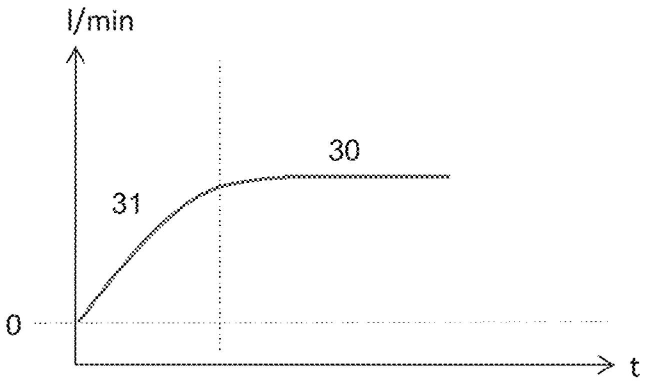
FIG. 2 shows a schematic flow profile of the system of FIG. 1.

FIG. 2 shows a schematic flow profile 30, 31 of the system for respiratory gas supply 1. Here the respiratory gas source 2 is controlled by the control unit 3 using the flow control module 6 for the specification of a respiratory gas flow 30 in the range of 0-90 l/min. It can be seen that the flow 30 gradually rises 31 and is finally held constant at the prescribed value 30.

The flow sensor device 8 determines the current flow and the control unit compares this with the specified flow and adjusts the specified flow 30 with a high level of accuracy of at least +/−5% in the flow range from 5 to 70 l/min. The specification is possible in the range from 0-90 l/min, preferably from 0-60 l/min in steps of, for example, 0.5 l/min. If desired by the user, an oxygen admixture of 0-90 l/min, preferably 1-45 l/min is possible. For this purpose, the control unit activates the oxygen source 14. In addition, the control unit always activates, when using the flow control module 6, the heater 16 and the humidifier 13 or the nebulizer 15 for purposes of conditioning the respiratory gas to a prescribable temperature and humidity. Temperature and humidity are typically always higher than those of the ambient air. The temperature can be set between 30° and 37° C., for example in 1° C. increments.

Figure 3:
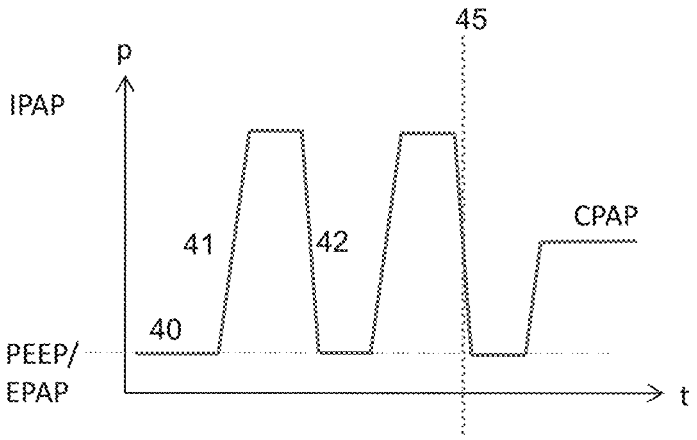
FIG. 3 shows schematically a pressure profile of the system of FIG. 1.

FIG. 3 shows schematically a pressure profile 40, 41 . . . of the system for respiratory gas supply 1. Here the respiratory gas source 2 is controlled by the control unit 3 using the pressure control module 4 to specify a respiratory gas pressure 40 in the range 0-90 mbar. It can be seen that the pressure 40 rises from a PEEP or EPAP level to an IPAP level.

The transition from the PEEP or EPAP level to the IPAP level can take place in the form of a prescribable ramp 41 or waveform. The transition from IPAP to EPAP can also take place in the form of a prescribable ramp 42 or waveform. The EPAP pressure can be constant or can increase from an initial low EPAP to the end of expiration. In accordance with the invention it is also conceivable that the EPAP could comprise at least two different levels of pressure.

The flow sensor device 8 and/or the pressure sensor device determines the current flow and/or pressure and from these values the control unit determines the respiratory phase of the patient and takes these into account, at least temporarily, when specifying the IPAP and EPAP pressures. The control unit compares the pressure with the prescribed pressure (from the memory 5) and adjusts the pressure with a high level of accuracy of at least +/−5% in the range from 2 to 45 mbar.

FIG. 3 also shows that on the basis of user selection 45, or an event 45, the control unit sets the pressure at a constant CPAP level. The event is recognized by the control unit, for example, from the signals of the flow sensor device 8 and/or the pressure sensor device, as interrupted respiration or as periodic respiration.

Figure 4:
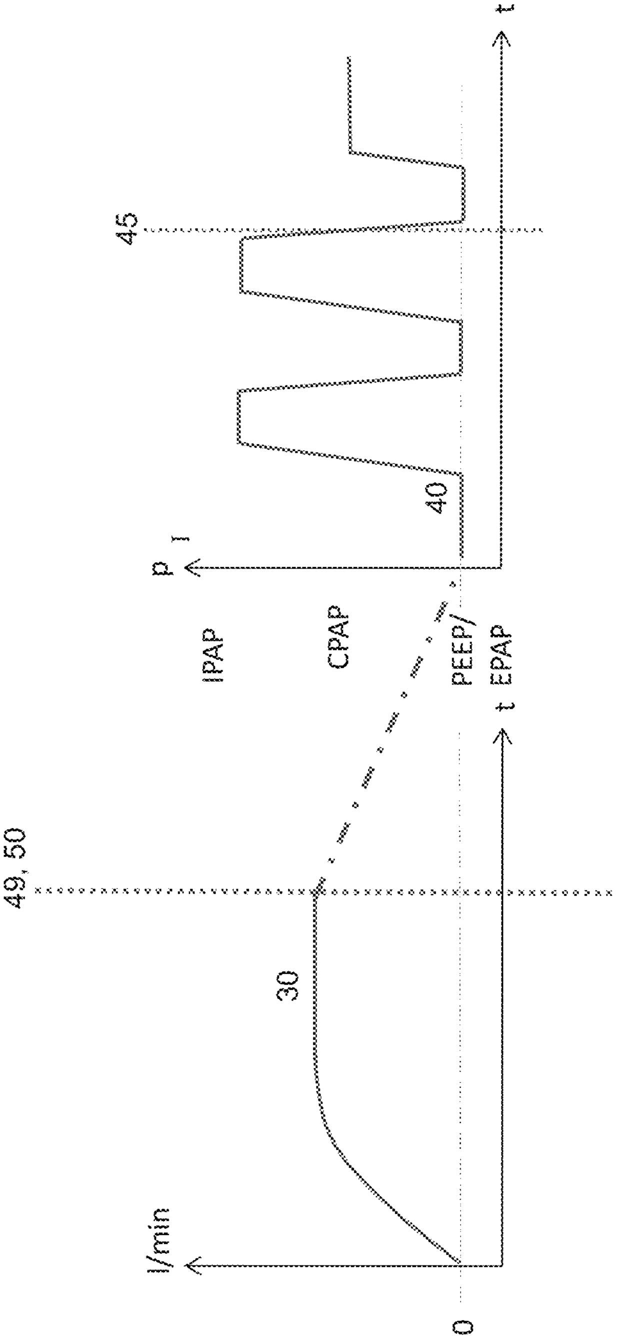
FIG. 4 shows a schematic flow profile and pressure profile of another respiratory gas supply system according to the instant invention.

FIG. 4 shows schematically a flow profile 30 of the system for respiratory gas supply 1. Here the respiratory gas source 2 is controlled by the control unit 3 using the flow control module 6 for the specification of a respiratory gas flow 30 in the range of 0-90 l/min. FIG. 4 also shows schematically a pressure profile 40 of the system for respiratory gas supply 1. Here the respiratory gas source 2 is controlled by the control unit 3 using the pressure control module 4 for the specification of a respiratory gas pressure 40 in the range from 0-90 mbar to EPAP or IPAP or CPAP pressure. FIG. 4 also shows that the control unit 3 alternately activates the flow control module 4 and then the pressure control module 4. The transition from flow control to pressure control or from pressure control to flow control can be made by user selection 49 via the user interface 9 or automatically at an event 50 specified by the control unit, or automatically in a prescribed sequence read from the memory 5 by the control unit. Such an event 50 can be the change of the time of day. For this purpose, the control unit has a clock that switches from a day mode to a night mode in accordance with the times that can be set. The control unit can initiate the change from day to night mode based on a user input, or based on a sensor device that detects the user's sleep. The control unit 3 can activate the flow control module, wherein these control the respiratory gas source 2 during the day so as to specify a respiratory gas flow. The control unit 3 registers the change of the time of day and at night activates the pressure control so as to specify a respiratory gas pressure with a low inspiratory pressure and a higher expiratory pressure or at a CPAP level.

The system in accordance with FIG. 4 is also set up and designed such that the control unit 3 activates the flow module 6 during the day, wherein the flow module 5 controls the respiratory gas source 2 so as to specify a respiratory gas flow and at night so as to specify at least one respiratory gas pressure level, which is modulated as a function of signals 20 from the pressure sensor device 7 and/or the flow sensor device 8, if the signals 20 are indicative of periodic respiration or interrupted respiration. If the signals 20 are indicative of periodic respiration the respiratory gas pressure level is modulated such that the pressures specified dampen or amplify the periodic respiration. If the signals 20 are indicative of interrupted respiration the respiratory gas pressure level is modulated such that the pressure specifications specify a higher pressure difference EPAP–IPAP or a CPAP.

The inventive high-flow system for respiratory gas supply uses a gas mixer to build up a fresh gas flow of up to 90 l/min, whereby the flow rate is higher than with respiratory equipment. As a result of the high flow, the respiratory gas flows continuously to the patient without hindering his or her own respiration. The system includes a gas mixer (compressed air or fan and oxygen), a respiratory tract humidifier (which heats the respiratory gas at the same time), possibly also a reservoir bag and a PEEP valve. The pressure generated by the PEEP valve at the end of expiration is also maintained during inspiration, since there is a high respiratory gas flow throughout the respiratory cycle. The high flow CPAP system reduces the risk of pressure inconsistencies using mask CPAP.

Figure 5:
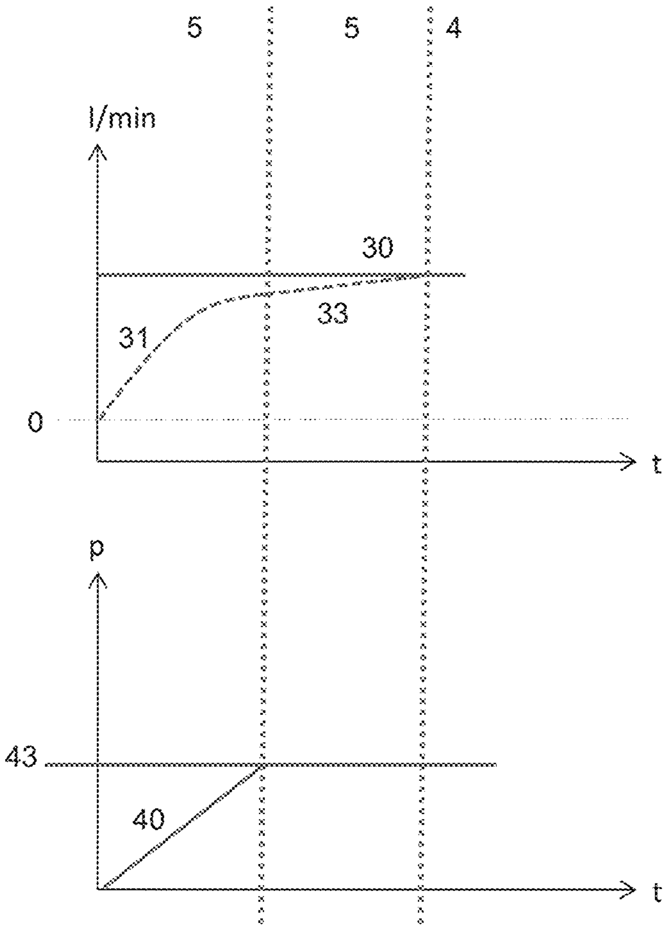
FIG. 5 shows a schematic flow profile and pressure profile of yet another respiratory gas supply system according to the instant invention.

The system in accordance with FIG. 5 is also set up and designed such that the control unit 3 activates the flow module 6, wherein the flow module 6 controls the respiratory gas source 2 so as to specify a prescribable respiratory gas flow 30 and increases the pressure 40 as a function of signals 20 from the pressure sensor device 7 and/or the flow sensor device 8 until the prescribed respiratory gas flow 30 is reached. The system is also set up such that the flow sensor device 8 monitors the respiratory gas flow, wherein the flow module 6 checks whether the prescribed respiratory gas flow has been reached on the basis of the signals of the flow sensor device 8, and wherein the pressure sensor device monitors the respiratory gas pressure, wherein the flow module 6 checks whether a prescribed maximum respiratory gas pressure 43 has been reached on the basis of the signals from the pressure sensor device, and the flow module 6 does not increase the maximum respiratory gas pressure further until the prescribed respiratory gas flow 30 has been reached. The current flow 33 can remain below the specified value 30 for a few seconds or minutes and increase only slowly if necessary. When the prescribed respiratory gas flow 30 is reached, a changeover to flow control module 4 can take place.

Figure 6:
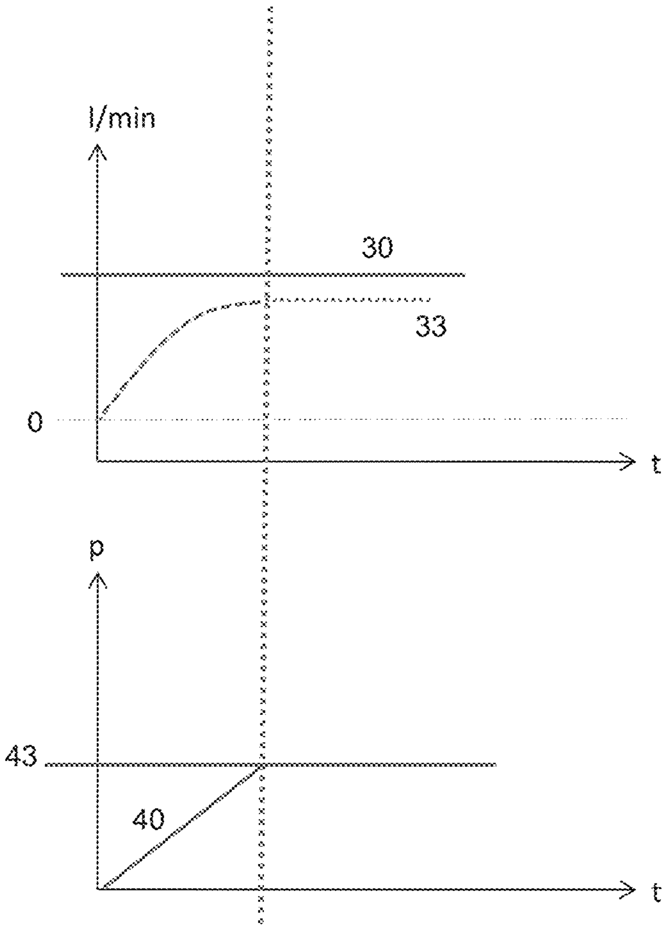
FIG. 6 shows a schematic flow profile and pressure profile of a still further respiratory gas supply system according to the instant invention.

The system in accordance with FIG. 6 is also set up and designed such that the control unit 3 activates the flow module 6, wherein the flow module 6 controls the respiratory gas source 2 for the specification of a prescribable respiratory gas flow 30 and increases the pressure 40 as a function of signals 20 from the pressure sensor device 7 and/or the flow sensor device 8 until the prescribed respiratory gas flow 30 is reached. The system is also set up such that the flow sensor device 8 monitors the respiratory gas flow, wherein the flow module 6 or the control unit 3 checks whether the specified respiratory gas flow has been reached on the basis of the signals from the flow sensor device 8, and wherein the pressure sensor device monitors the respiratory gas pressure, wherein the flow module 6 or the control unit 3 checks whether a prescribed maximum respiratory gas pressure 43 is reached on the basis of the signals from the pressure sensor device, and the flow module 6 or the control unit 3 does not increase the maximum respiratory gas pressure further if the prescribed respiratory gas flow 30 is not reached. The maximum respiratory gas pressure 43 is not increased further even if the current respiratory gas flow 33 has not reached the specified value 30.

What is claimed is:

1. A system for supplying respiration gas, wherein the system comprises a respiration gas source;

a memory for storing specified parameters;

a pressure sensor device configured to provide a pressure signal;

a flow sensor device configured to provide a flow signal;

a user interface configured for specifying parameters of the respiratory gas supply or for data exchange;

a control unit configured to operate in (i) a pressure control mode in which the respiration gas source is actuated to specify a respiration gas pressure as Expiratory Positive Airway Pressure (EPAP) and an inspiratory pressure as Inspiratory Positive Airway Pressure (IPAP) that is higher than the EPAP, or (ii) a flow control mode in which the respiration gas source is actuated to specify a respiration gas flow, based on a specification input by a user via the user interface or automatically based on information stored in the memory, the control unit being further configured to recognize interrupted breathing from the pressure signal and/or the flow signal;

a patient interface;

a respiratory gas tube for delivering respiratiory gas from the respiration gas source to the patient interface;

a humidifier and/or an oxygen source and/or a nebulizer and/or a heater;

and wherein the respiration gas source is actuated for flow control with the control unit specifying the respiration gas flow while the user is awake and for pressure control with the control unit specifying at least one respiration gas pressure level that is modulated depending on the pressure signal and/or the flow signal while the user is asleep, wherein the respiration gas pressure level—when interrupted breathing is recognized—is modulated such that the control unit specifies a higher difference between EPAP and IPAP, wherein the control unit is further configured to attempt to generate a set respiration gas flow when the flow control mode is activated, wherein a respiration gas pressure required for generating the set respiration gas flow is determined, wherein—when the respiration gas pressure required for generating the set respiration gas flow reaches a specified threshold for a determined period of time—a switch to the pressure control mode takes place and a specified maximum permissible respiration gas pressure is maintained even when a generated respiration gas flow is below the set respiration gas flow, and—when the set respiration gas flow is again reached or exceeded for a determined period of time—a switch back to the flow control mode takes place, and wherein the EPAP level comprises at least two pressure levels and increases from an initially low EPAP toward an EPAP at an end of expiration.

2. The system of claim 1, wherein in the pressure control mode the respiration gas source is actuated to specify a ramp-shaped pressure increase from an expiratory pressure level to an inspiratory pressure level and to specify a ramp-shaped pressure drop from the inspiratory pressure level to the expiratory pressure level.

3. The system of claim 1, wherein in the pressure control mode the respiration gas source is actuated to specify the inspiratory pressure with a specifiable pressure waveform and to specify the expiratory pressure with a specifiable pressure waveform.

4. The system of claim 1, wherein in the pressure control mode the respiration gas source is actuated to specify the inspiratory pressure at two different inspiratory pressure levels and to specify the expiratory pressure at two different expiratory pressure levels.

5. The system of claim 1, wherein the control unit is configured to actuate the respiration gas source to specify a specifiable respiration gas flow and, depending on the pressure signal and/or the flow signal, to increase the respiration gas pressure until the specified respiration gas flow has been reached.

6. The system of claim 1, wherein the flow sensor device is configured to monitor the respiration gas flow and the pressure sensor device is configured to monitor the respiration gas pressure, the control unit is configured to actuate the respiration gas source to specify a specifiable respiration gas flow and, based on the flow signal, to check whether the specified respiration gas flow has been reached and, based on the pressure signal, to check whether a specified maximum respiration gas pressure has been reached, and wherein the control unit does not increase the specified maximum respiration gas pressure further when the specified respiration gas flow is not reached.

7. The system of claim 1, wherein the system is configured to regulate an amount of supplied respiration gas via a flow meter and to set application of a desired amount of oxygen via an oxygen mixer.

8. The system of claim 1, wherein the system is configured to deactivate an internal oxygen source when the flow control mode is activated and in this case to use an external oxygen source.

9. The system of claim 1, wherein the system is configured such that a pulse oximeter or a CO2 measuring device is adaptable and is configured to communicate with the pulse oximeter or CO2 measuring device and/or to supply the pulse oximeter or the CO2 measuring device with energy.

10. The system of claim 9, wherein the system is configured to set a flow rate and an oxygen admixture using an automatic algorithm via measured values of the pulse oximeter and/or the CO2 measuring device.

11. The system of claim 9, wherein the control unit takes account of measured values of the pulse oximeter and/or the CO2 measuring device when an oxygen source and/or the flow control mode is activated and/or controlled.

12. The system of claim 1, wherein the system is configured to raise the respiration gas pressure level from a PEEP or EPAP level to an IPAP level in the form of a specifiable ramp or waveform and to lower the respiration gas pressure level from the IPAP to the EPAP level in the form of a specifiable ramp or waveform.

13. The system of claim 1, wherein the control unit is configured, when the flow control mode is activated, to determine which breathing phase is present, and to recognize fluctuations throughout breathing and to attempt to continuously compensate for the fluctuations.

* * * * *